United States Patent
Lapen et al.

(10) Patent No.: US 7,186,522 B2
(45) Date of Patent: Mar. 6, 2007

(54) PAPANICOLAU STAINING PROCESS

(75) Inventors: Daniel Lapen, Lancaster, MA (US);
Norman Soule, Brockton, MA (US);
Somthouk Lim, Farmingham, MA (US)

(73) Assignee: CYTYC Corporation, Marlborough, MA (US)

( * ) Notice: Subject to any disclaimer, the term of this patent is extended or adjusted under 35 U.S.C. 154(b) by 458 days.

(21) Appl. No.: 10/404,879

(22) Filed: Mar. 31, 2003

(65) Prior Publication Data

US 2004/0191854 A1    Sep. 30, 2004

(51) Int. Cl.
*G01N 1/30* (2006.01)
*G01N 33/48* (2006.01)
(52) U.S. Cl. .................................... 435/40.5
(58) Field of Classification Search ............. 435/40.5; 510/406
See application file for complete search history.

(56) References Cited

U.S. PATENT DOCUMENTS

| 6,143,512 A | 11/2000 | Markovic et al. |
| 2002/0019001 A1 | 2/2002 | Light |

OTHER PUBLICATIONS

PCT International Search Report for PCT/US2004/09437, Applicant: Cytyc Corporation, Forms PCT/ISA/210 and 220, dated Mar. 24, 2005 (4 pages).
PCT Written Opinion of the International Search Authority for PCT/US2004/09437, Applicant: Cytyc Corporation, Form PCT/ISA/237, dated Mar. 24, 2005 (5 pages).

*Primary Examiner*—Ralph Gitomer
*Assistant Examiner*—Kailash C. Srivastava
(74) *Attorney, Agent, or Firm*—Vista IP Law Group LLP

(57) ABSTRACT

A method for treating a biological sample with a Papanicolaou staining process is provided. The method comprises incorporating a detergent treatment into the staining process at any of various steps. The method has been found to advantageously reduce the number of artifacts produced during Papanicolaou staining. Also provided is a sample stained by such a process.

18 Claims, 1 Drawing Sheet

PAPANICOLAU STAINING PROCESS

TECHNICAL FIELD

This invention relates to methods, articles and compositions useful in staining biological samples.

BACKGROUND OF THE INVENTION

Medical diagnostic testing methods are critical screening tools for the early detection of pathological conditions. Early detection permits the identification of such conditions at a stage when successful treatment is more likely. Early treatment also frequently involves less damaging or less invasive treatment methods and decreases the impact on the patient. In addition to routine screening, diagnostic testing is also used in a variety of other applications, including biopsy analysis and monitoring the results of ongoing medical treatment.

One particularly useful tool in diagnostic testing is the Papanicolaou staining process. This process was first developed for the staining of gynecological specimens, and has led to a dramatic decrease in the fatality rate from cervical cancer. Papanicolaou staining is now used in diagnosing a variety of pathological conditions from many different tissues and organs.

However, Papanicolaou staining is subject to artifacts that can adversely affect the ability of a technologist or machine to successfully read a processed sample. These artifacts include spurious non-specific cytoplasmic staining, artifacts such as cytoplasmic cracking, cornflaking, smudged nuclear detail, hypochromatic staining and hyperchromatic staining. Such artifacts, at a minimum, reduce the fraction of the sample which can be evaluated, can produce false staining patterns that interfere with accurate diagnosis, and may render the sample unreadable. Difficulties in analyzing such samples leads to an increase in patient anxiety, rescreening costs, delays in diagnosis and, more importantly, potential misdiagnosis.

There is a need in the art for improved procedures for staining diagnostic specimens, and for compositions and articles of manufacture useful in such methods.

SUMMARY OF THE INVENTION

An improved method for treating a biological sample with a Papanicolaou staining process is provided. The method comprises incorporating a detergent treatment into the staining process at any of various steps. The method has been found to advantageously reduce the number of artifacts produced during Papanicolaou staining. Also provided is a sample stained by such a process.

DETAILED DESCRIPTION OF THE INVENTION

Figure 1:
FIG. 1 shows a sample stained with a Papanicolaou staining process.

The inventors have advantageously discovered that incorporation of a detergent treatment into a Papanicolaou staining procedure reduces the occurrence of artifacts to which the procedure is susceptible. Use of a detergent has been found to clear excess stain from the cytoplasm of cells stained by this procedure, allowing for increased contrast and improved ability to detect cellular, nuclear and chromatin morphology. Additionally, the removal of excess stain from the cytoplasm may lead to an increased ability to detect hyperchromasia associated with abnormality.

The term "Papanicolaou staining process," "pap stain," "pap test" and the like refer to a modified or unmodified Papanicolaou staining procedure which differentially stains cell nuclei and cytoplasm in a sample, for example a sample obtained during a gynecological screening examination such as a pap smear.

The test relies on the ability to distinguish the staining pattern, staining intensity and the size and shape of the nucleus and cytoplasm of different cell types within the sample. The Papanicolaou staining process advantageously provides dark stained nuclei and transparent cytoplasms, which is particularly useful in detecting abnormal cells within multi-layered samples provided by certain sampling techniques including pap smears.

A usable test depends on the ability to read a significant percentage of cells in the sample, otherwise test accuracy may be comprised and samples may be rendered unusable, leading to additional rescreening costs and increased patient anxiety.

Consequently, staining artifacts which reduce the ability to discern the true staining pattern of cells in a sample can dramatically impair the usefulness of a pap test. Artifacts can reduce the ability to differentiate between the staining pattern of the nucleus and the cytoplasm, can increase the percentage of cells or sample area which are unreadable, and can increase cytoplasmic staining thereby diminishing the transparency that is one of the primary advantages of the pap test, thus making it more difficult to distinguish abnormal cells within the sample.

Before the present invention is described in further detail, it is to be understood that this invention is not limited to the particular methodology, solutions or apparatuses described, as such methods, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a sample" includes a plurality of samples, reference to "a detergent" includes a plurality of such detergents, reference to "a counterstain" includes a plurality of counterstains, and the like. Additionally, use of specific plural references, such as "two," "three," etc., read on larger numbers of the same subject unless the context clearly dictates otherwise.

Terms such as "connected," "attached," and "linked" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed.

Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

The term "optional" or "optionally" means that the subsequently described event or circumstance may or may not occur, and includes instances where the event or circumstance occurs and instances in which it does not.

Papanicolaou Staining

A Papanicolaou staining process comprises at least a hematoxylin staining step, an Orange G cytoplasmic counterstaining step, and an Eosin Y-light green/fast green counterstaining step. The process may incorporate a "bluing" step Pap staining advantageously produces a sample with transparent cell cytoplasms which is particulary useful for analysis of cells covering multiple layers such as those obtained from a pap smear.

Prior to commencing a Papanicolaou staining process, the sample must be fixed. Any fixation method producing satisfactory results may be used. Typically an alcoholic fixation is used with pap staining, e.g. 95% ethanol, 100% methanol, 80% propanol, or 95% ethanol/ether (1:1). Commercial spray fixatives may also be used.

A typical Papanicolaou staining process comprises a hematoxylin staining step in combination with a metal mordant to stain the chromatin of cells, and may be done progressively or regressively. The chromatin staining is a critical portion of this test, as the size, staining intensity and staining pattern of the chromatin is a critical element in the analysis of abnormal cells within the sample. Any form of hematoxylin may be used, including Harris's, Gill's, Delafield's, Ehrlich's or Mayer's hematoxylin. Substitutes for hematoxylin utilizing dyes e.g. Thionin, Victoria Blue B, Azure B, etc. may also be used.

If done regressively, the sample is overstained and then differentiated with an agent (e.g., dilute HCl) which allows the staining intensity to be reduced to the desired level. This causes the staining color to shift from blue/purple to salmon pink/red. A "bluing" step may be used to reestablish the blue color using an agent as known in the art (e.g., Scott's tap water substitute, ammonia water, lithium carbonate). The bluing solution can be incorporated without a differentiation step.

Multiple cytoplasmic counterstains are used in Papanicolaou staining to allow identification of the various cell types in the sample, their morphology and their frequency.

The cytoplasmic stains Orange G and Eosin Y—Light Green/Fast Green are prepared in alcohol. Orange G is a monochromatic stain that stains cell cytoplasms yellow or orange if keratin is present, allowing for the distinction of mature or maturing keratin-producing malignant cells from the less conspicuous benign cells. Orange G can be used in the form of a solution known in the art of cell staining, for example as OG-6.

Traditionally, Eosin Y—Light Green/Fast Green is prepared as a mixture of three stains, Eosin Y—Light Green SF and/or Fast Green FCF, and Bismarck Brown. Exemplary mixtures include EA36, EA50, and EA65. Eosin Y produces a pink color in nucleoli, cilia, red blood cells and the cytoplasm of mature squamous cells. Light Green SF Yellowish and Fast Green FCF produce a blue/green color in the cytoplasm of metabolically active parabasal squamous cells, intermediate squamous cells and columnar cells. Bismarck Brown does not produce a useable staining pattern in pap staining, and can be excluded in variations of the method. Substitutes for Light Green SF Yellowish may also be used, e.g. Fast Green FCF. Cytoplasmic counterstains can also be a mixture of OG and Eosin Y—Light Green/Fast Green resulting in a single solution for use as a counterstain.

The alcohol in which these cytoplasmic counterstains are prepared results in the transparent cytoplasms so useful in analyzing samples stained by the Papanicolaou process.

Wash steps are incorporated into the staining procedure as appropriate, as are hydration/dehydration series when transferring between aqueous and nonaqueous solutions. Upon completion of the staining process, the samples can be cleared and mounted, as is known in the art. Additional procedures may be performed on the samples prior or subsequent to the Papanicolaou procedure. The samples can then be analyzed manually and/or by a suitable apparatus, for example an automated imaging system. Exemplary automated imaging systems include Cytyc Corporation's ThinPrep® Imaging System, the TriPath FocalPoint™ Profiler, the ChromaVision Acis® System, the CompuCyt iCyte Imaging System, the Applied Imaging CytoVision™ System, and the Veracel Verasys Imaging System.

A variety of modifications to the Papanicolaou staining procedure may be made, and are known in the art. For example, the process may be modified as described in U.S. Pat. Nos. 5,168,066 and 6,348,325 (issued Dec. 1, 1992 and Feb. 19, 2002, respectively, and assigned to Cytyc Corp.) to incorporate the use of thionin. Other thiazin dyes and triarylmethane dyes can be used.

The Sample

The portion of the sample to be analyzed can be any source of biological material that can be obtained from a living organism directly or indirectly, including cells, tissue or fluid. Nonlimiting examples of the sample include blood, urine, semen, milk, sputum, mucus, plueral fluid, pelvic fluid, sinovial fluid, ascites fluid, body cavity washes, eye brushing, skin scrapings, a buccal swab, a vaginal swab, a pap smear, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, and samples of in vitro cell culture constituents. Typically the sample will be a pap smear as is routinely obtained during a gynecological examination or a biopsy suspected of containing abnormal cells.

The sample can be a positive control sample which is known to contain abnormal cells. A negative control sample can also be used which is used to determine whether a given set of staining conditions produces false positives (a positive signal even in the absence of abnormal cells in the sample).

Typically the sample is provided for staining on a slide or similar glass surface, for example a vial, cover slip, or other surface that is transparent to the incident light used for its analysis.

The Detergent

Any detergent which detectably reduces artifacts produced during a Papanicolaou staining procedure can be used. The detergent is used in an amount and for a time suitable to detectably reduce such artifacts. The percentage of at least one such artifact can desirably be reduced at least about 10%, 20%, 30%, 40%, 50%, 70%, 90%, 95%, 98% or more by incorporating a detergent wash as described herein. When used in imaging systems which select certain areas of the slide ("fields of interest") to be analyzed based on any of a variety of parameters as is known in the art, the invention desirably decreases the number of falsely selected fields (which are falsely selected for analysis based on staining artifacts that meet the selection criteria of the imaging system) at least about 10%, 20%, 30%, 40%, 50%, 70%, 90%, 95%, 98% or more. This increases the percentage of useful fields selected for analysis.

The detergent may be non-ionic, cationic, anionic or zwitterionic. Mixtures of detergents may also be used. Exemplary classes of detergents include alcohol ether sulfates, alcohol sulfates, alkanolamides, alkyl sulfonates, amine oxides, amphoteric detergents, anionic detergents, betaine derivatives, cationic detergents, disulfonates, dodecylbenzene sulfonic acid, ethoxylated alcohols, ethoxylated alkyl phenols, ethoxylated fatty acids, glycerol esters hydrotropes, lauryl sulfates, mono and diglycerides, non-ionic detergents, phosphate esters, quaternary detergents, and sorbitan derivatives.

Exemplary non-ionic detergents include BigCHAP(N,N-Bis[3-(D-gluconamido)propyl]cholamide), Bis(polyethylene glycol bis[imidazoyl carbonyl]), Brij® 30 (Polyoxyethylene 4 lauryl ether) Brij® 35 (Polyoxyethylene 23 lauryl ether), Brij® 52 (Polyoxyethylene 2 cetyl ether), Brij® 56 (Polyoxyethylene 10 cetyl ether), Brij® 58 (Polyoxyethylene 20 cetyl ether), Brij® 72 (Polyoxyethylene 2 stearyl ether), Brij® 76 (Polyoxyethylene 10 stearyl ether), Brij® 78 (Polyoxyethylene 20 stearyl ether), Brij® 92 (Polyoxyethylene 2 oleyl ether), Brij® 97 (Polyoxyethylene 10 oleyl ether), Brij® 98 (Polyoxyethylene 20 oleyl ether), Brij® 700 (Polyoxyethylene 100 stearyl ether), Cremophor® EL (castor oil/ethylene oxide polyether), Decaethylene glycol monododecyl ether, octanoyl-N-methylglucamide (MECA-8), decanoyl-N-methylglucamide (MECA-10), n-octylglucoside, n-dodecylglucoside, isotridecyl-poly(ethyleneglycolether)$_n$, N-Decanoyl-N-methylglucamine, n-Decyl α-D-glucopyranoside, Decyl β-D-maltopyranoside, n-Dodecanoyl-N-methylglucamide, n-Dodecyl α-D-maltoside, n-Dodecyl β-D-maltoside, Heptaethylene glycol monodecyl ether, Heptaethylene glycol monotetradecyl ether, n-Hexadecyl β-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630 (Octylphenyl-polyethylene glycol), Igepal® CA-210 (polyoxyethylene(2) isooctylphenyl ether), Igepal® CA-520 (polyoxyethylene(5) isooctylphenyl ether), Igepal® CO-630 (polyoxyethylene(9)nonylphenyl ether), Igepal® CO-720 (polyoxyethylene(12) nonylphenyl ether), Igepal® CO-890 (polyoxyethylene(40) nonylphenyl ether), Igepal® CO-990 (polyoxyethylene(100) nonylphenyl ether), Igepal® DM-970 (polyoxyethylene(150) dinonylphenyl ether), Methyl-6-O-(N-heptylcarbamoyl)-α-D-glucopyranoside, Nonaethylene glycol monododecyl ether, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin, Span® 20 (Sorbitan monolaurate), Span® 40 (Sorbitan monopalmitate), Span® 60 (Sorbitan monostearate), Span® 65 (Sorbitan tristearate), Span® 80 (Sorbitan monooleate), Span® 85 (Sorbitan trioleate), Tergitol in any form (including Types 15-S-5, 15-S-7, 15-S-9, 15-S-12, 15-S-30, NP-4, NP-7, NP-9, NP-10, NP-40, NPX (Imbentin-N/63), TMN-3 (Polyethylene glycol trimethylnonyl ether), TMN-6 (Polyethylene glycol trimethylnonyl ether), TMN-10 (Polyethylene glycol trimethylnonyl ether), MIN FOAM 1×, and MIN FOAM 2×), Tetradecyl-β-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton® CF-21, Triton® CF-32, Triton® DF-12, Triton® DF-16, Triton® GR-5M, Triton® N-101 (Polyoxyethylene branched nonylphenyl ether), Triton® QS-15, Triton® QS-44, Triton® RW-75 (Polyethylene glycol 260 mono (hexadecyl/octadecyl) ether and 1-Octadecanol), Tritone® X-100 (Polyethylene glycol tert-octylphenyl ether), Triton® X-102, Triton® X-15, Triton® X-151, Triton® X-200, Triton® X-207, Triton® X-114, Triton® X-165, Triton® X-305, Triton® X-405 (polyoxyethylene(40) isooctylphenyl ether), Triton® X-405 reduced (polyoxyethylene(40) isooctylcyclohexyl ether), Triton® X-45 (Polyethylene glycol 4-tert-octylphenyl ether), Triton® X-705-70, TWEEN® in any form (including TWEEN® 20 (Polyoxyethylenesorbitan monolaurate), TWEEN® 21 (Polyoxyethylenesorbitan monolaurate), TWEEN® 40 (polyoxyethylene(20) sorbitan monopalmitate), TWEEN® 60 (Polyethylene glycol sorbitan monostearate), TWEEN® 61 (Polyethylene glycol sorbitan monostearate), TWEEN® 65 (Polyoxyethylenesorbitan Tristearate), TWEEN® 80 (Polyoxyethylenesorbitan monooleate), TWEEN® 81 (Polyoxyethylenesorbitan monooleate), and TWEEN® 85 (polyoxyethylene(20) sorbitan trioleate)), Tyloxapol (4-(1,1,3,3-tetramethylbutyl) phenol polymer with formaldehyde and oxirane), and n-Undecyl β-D-glucopyranoside.

Exemplary anionic detergents include Chenodeoxycholic acid, Cholic acid, Dehydrocholic acid, Deoxycholic acid, Digitonin, Digitoxigenin, N,N-Dimethyldodecylamine N-oxide, Sodium docusate, Sodium glycochenodeoxycholate, Glycocholic acid, Glycodeoxycholic acid, Glycolithocholic acid 3-sulfate disodium salt, Glycolithocholic acid ethyl ester, N-Lauroylsarcosine, Lithium dodecyl sulfate, Lugol (Iodine Potassium Iodide), Niaproof (2-Ethylhexyl sulfate sodium salt), Niaproof 4 (7-Ethyl-2-methyl-4-undecyl sulfate sodium salt), optionally substituted alkylsulfonate salts (including salts of 1-butanesulfonate, pentanesulfonate, hexanesulfonate, 1-Octanesulfonate, 1-decanesulfonate, 1-dodecanesulfonate, 1-heptanesulfonate, 1-heptanesulfonate, 1-nonanesulfonate, 1-propanesulfonate, and 2-bromoethanesulfonate, especially the sodium salts), Sodium cholate, Sodium deoxycholate, optionally substituted Sodium dodecyl sulfate, Sodium octyl sulfate, Sodium taurocholate, Sodium taurochenodeoxycholate, Sodium taurohyodeoxycholate, Taurolithocholic acid 3-sulfate disodium salt, Tauroursodeoxycholic acid sodium salt, Trizma® dodecyl sulfate, Ursodeoxycholic acid. The anionic detergent can be provided in acid or salt form, or both.

Exemplary cationic detergents include Alkyltrimethylammonium bromide, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Ethylhexadecyldimethylammonium bromide, Girard's reagent T, Hexadecyltrimethylammonium bromide, N,N',N'-Polyoxyethylene(10)-N-tallow-1,3-diaminopropane, Thonzonium bromide, and Trimethyl(tetradecyl) ammonium bromide.

Exemplary zwitterionic detergents include CHAPS (3-{(3-cholamidopropyl)-dimethylammonio}-1-propane-sulfonate), CHAPSO (3-{(3-cholamidopropyl)dimethyl-ammonio}-2-hydroxy-1-propane-sulfonate), 3-(Decyldimethylammonio)propanesulfonate, 3-(Dodecyldimethylammonio)propanesulfonate, 3-(N,N-Dimethylmyristylammonio)propanesulfonate, 3-(N,N-Dimethyloctadecylammonio)propanesulfonate, 3-(N,N-Dimethyloctylammonio)propanesulfonate, and 3-(N,N-Dimethylpalmitylammonio)propanesulfonate.

The detergent includes those known or discoverable in the art. The detergent can be synthesized or can be obtained commercially from any of a variety of vendors (e.g., Sigma-Aldrich Corp., St. Louis, Mo., USA, www.sigrnaaldrich.com). Benzalkonium chloride and CHAPS have been found to be particularly useful in reducing artifacts during Papanicolaou staining.

A given detergent may be tested for its ability to reduce artifacts by incorporation into a wash step in a Papanicolaou staining process, which may be performed under conditions known to produce staining artifacts. The sample treated with test detergent may then be evaluated against a sample processed without a detergent treatment, and against a sample processed with a benzalkonium chloride treatment or other positive control treatment known to reduce staining artifacts.

Typically the amount of detergent used will be at least about 0.0001% and up to about 10% of the solution in which it is to be used, and may be at least about 0.0005%, 0.001%, 0.005%, 0.01%, 0.05%, 0.1%, 0.2%, 0.5% or 1% or more of the solution; the amount of the detergent may be about 5% or less, about 2.5% or less, about 2% or less, about 1% or less, about 0.5% or less, about 0.2% or less, about 0.1% or less, about 0.05% or less of the solution, or any range or subrange therebetween.

The detergent treatment may be performed at any pH which permits the reduction of artifacts while not adversely affecting the ability to analyze the sample. Thus the detergent treatment may be performed at about pH 1, 2, 3, 4, 5, 6, 7, 8, 9, 10, 11, 12, 13 or within any range or subrange therebetween. Typically the treatment will be performed at a pH of about 2 to about 10.

The detergent may be used at any point in a Papanicolaou staining process. For example, the detergent may be used prior to the hematoxylin stain, mixed with the hematoxylin stain, after the hematoxylin stain, combined with a bluing solution, after the bluing solution, or combined with the Orange G, Eosin Y—Light Green/Fast Green or other counterstain solutions.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Cytoplasmic cracking was found to be very visible on pap smear slides processed under test Papanicolaou staining conditions. To test methods for reducing cytoplasmic cracking, 4 different sample pap smears were obtained, slides were made from the samples, fixed, allowed to dry for one day, and then stained with a modified Pap stain according to the procedure below:

Steps: 1 Start Station
  2 Test wash step
  3 5 min 50% Reagent alcohol
  4 5 min Salt Solution (10% NaCl in 50% alcohol)
  5 5 min Salt Solution (10% NaCl in 50% alcohol
  6 1 min 95% Reagent alcohol
  7 1 min 95% Reagent alcohol
  8–22 1 min Nuclear stain (15 min)
  23 20 sec Isopropyl alcohol
  24 20 sec Isopropyl alcohol
  25 30 sec Isopropyl alcohol
  26 20 sec Isopropyl alcohol
  27–34 1 min Counterstain (mixture of Orange G and eosin Fast Green/Light Green) (8 min)
  35 30 sec 100% Reagent alcohol
  36 3 min Isopropyl alcohol
  37 3 min Isopropyl alcohol
  38 1 min Xylene
  39 3 min Xylene
  40 End Xylene
    Remove slides to final xylene
    Coverslip manually using Permount The four samples produced cytoplasmic cracking and were subjected to test wash steps to determine conditions which might reduce the artifact. Ten slides were prepared from each sample. Five and fifteen minute water washes as well as fifteen minute washes with FC120 surfactant (3M Corporation) and FC170 surfactant (3M Corporation) were separately performed on the ten slides from each sample. Neither of these wash conditions was found to dramatically reduce the staining artifact of cytoplasmic cracking.

Ten additional slides were prepared from each of the four samples and subjected to further test wash steps, including fifteen minute washes in either FC170 0.1% pH 6.9, Tween® 80 0.1% pH 6.9, Igepal CA-630 0.1% pH 7.0, CHAPS 0.1% pH 7.7, ZEPHIRAN® 0.1% pH 7.2, water, water with no 50% alcohol step before the salt solution step, water with no salt solution step, and water with no 50% alcohol step before the salt solution step and no salt solution steps.

ZEPHIRAN® (benzalkonium chloride) dramatically reduced spurious blue cytoplasmic staining and reduced cytoplasmic cracking. CHAPS® also reduced both artifacts to a certain degree at this concentration. The other treatments at the indicated concentrations had little effect on these staining artifacts.

Example 2

An example of a Papanicolaou staining protocol incorporating a detergent wash step is given below:

| Steps | Reagent | Time |
| --- | --- | --- |
| 1 | Distilled water | 5 min |
| 2 | Nuclearstain | 5 min |
| 3 | Distilled Water | dH2O/10 sec |
| 4 | Rinse solution (detergent) | 20 sec |
| 5 | Distilled water | 30 sec |
| 6 | Bluing agent | 30 sec |
| 7 | Distilled water | 30 sec |
| 8 | 50% Reagent alcohol | 30 sec |
| 9 | 95% Reagent alcohol | 30 sec |
| 10 | Orange G | 1 min |
| 11 | 95% Reagent alcohol | 15 sec |
| 12 | 95% Reagent alcohol | 15 sec |
| 13 | EA Solution | 4 min |
| 14 | 95% Reagent alcohol | 1 min |
| 15 | 95% Reagent alcohol | 1 min |
| 16 | 100% Reagent alcohol | 30 sec |
| 17 | 100% Reagent alcohol | 30 sec |
| 18 | 100% Reagent alcohol | 30 sec |
| 19 | Xylene | 1 min |
| 20 | Xylene | 3 min |
| 21 | Xylene | End |

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. A process of staining a fixed biological sample, comprising in the following order:
   (a) contacting the sample with a hematoxylin stain,
   (b) contacting the sample with a detergent of a type and in an amount sufficient to reduce a staining artifact,
   (c) contacting the sample with an Orange G counterstain, and
   (d) contacting the sample with an Eosin Y- Light Green/ Fast Green counterstain.

2. The method of claim 1, comprising contacting the sample with the detergent in combination with a bluing agent.

3. The method of claim 1, wherein the sample is contacted with the detergent in a solution at a concentration of at least about 0.0001% and less than about 10% of the solution.

4. The method of claim 3, wherein the detergent is at least about 0.01% of the solution.

5. The method of claim 3, wherein the detergent is at least about 0.1% of the solution.

6. The method of claim 3, wherein the detergent is at least about 0.5% of the solution.

7. The method of claim 1, wherein the detergent is less than about 1% of the solution.

8. The method of claim 1, wherein the detergent is selected from the group consisting of alcohol ether sulfates, alcohol sulfates, alkanolamides, alkyl sulfonates, amine oxides, amphoteric detergents, anionic detergents, betaine derivatives, cationic detergents, disulfonates, dodecylbenzene sulfonic acid, ethoxylated alcohols, ethoxylated alkyl phenols, ethoxylated fatty acids, glycerol esters hydrotropes, lauryl sulfates, mono and diglycerides, non-ionic detergents, phosphate esters, quaternary detergents, and sorbitan derivatives.

9. The method of claim 1, wherein the detergent is a nonionic detergent.

10. The method of claim 9, wherein the non-ionic detergent is selected from the group consisting of Big-CHAP (N, N-Bis[3-(D-gluconamido) propyl] cholamide), Bis (polyethylene glycol bis [imidazoyl carbonyl]), Brij 30 (Polyoxyethylene 4 lauryl ether) Brij 35 (Polyoxyethylene 23 lauryl ether), Brij 52 (Polyoxyethylene 2 cetyl ether), Brij 56 (Polyoxyethylene 10 cetyl ether), Brij 58 (Polyoxyethylene 20 cetyl ether), Brij 72 (Polyoxyethylene 2 stearyl ether), Brij 76 (Polyoxyethylene 10 stearyl ether), Brij 78 (Polyoxyethylene 20 stearyl ether), Brij 92 (Polyoxyethylene 2 oleyl ether), Brij 97 (Polyoxyethylene 10 oleyl ether), Brij 98 (Polyoxyethylene 20 oleyl ether), Brij 700 (Polyoxyethylene 100 stearyl ether), Cremophor EL (castor oil/ethylene oxide polyether), Decaethylene glycol monododecyl ether, octanoyl-N-methylglucamide (MECA-8), decanoyl-N-methylglucamide (MECA-10), n-octylglucoside, n-dodecylglucoside, isotridecyl-poly(ethyleneglycolether)$_n$, N-Decanoyl-N-methylglucamine, n-Decyl α -D-glucopyranoside, Decyl β-D-maltopyranoside, n-Dodecanoyl-N-methylglucamide, n-Dodecyl α-D-maltoside, n-Dodecyl β-D-maltoside, Heptaethylene glycol monodecyl ether, Heptaethylene glycol monotetradecyl ether, n-Hexadecyl β-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630 (Octylphenyl-polyethylene glycol), Igepal CA-210 (polyoxyethylene(2) isooctylphenyl ether), Igepal CA-520 (polyoxyethylene(5) isooctylphenyl ether), Igepal CO-630 (polyoxyethylene(9)nonylphenyl ether), Igepal CO-720 (polyoxyethylene(12) nonylphenyl ether), Igepal CO-890 (polyoxyethylene(40) nonylphenyl ether), Igepal CO-990 (polyoxyethylene(100) nonylphenyl ether), Igepal DM-970 (polyoxyethylene(150) dinonylphenyl ether), Methyl-6-O-(N-heptylcarbamoyl-)-α-D-glucopyranoside, Nonaethylene glycol monododecyl ether, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl), Polyoxyethylene 25 propylene glycol stearate, Saponin, Span 20 (Sorbitan monolaurate), Span 40 (Sorbitan monopalmitate), Span 60 (Sorbitan monostearate), Span 65 (Sorbitan tristearate), Span 80 (Sorbitan monooleate), Span 85 (Sorbitan trioleate), a Tergitol, Tetradecyl-β-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-SM, Triton N-101 (Polyoxyethylene branched nonylphenyl ether), Triton QS-15, Triton QS-44, Triton RW-75 (Polyethylene glycol 260 monoChexadecyl/octadecyl) ether and 1-Octadecanol), Triton X-100 (Polyethylene glycol tert-octylphenyl ether), Triton X-102, Triton X-15, Triton X-151, Triton X-200, Triton X-207, Triton X-114, Triton X-165, Triton X-305, Triton X-405 (polyoxyethylene (40) isooctylphenyl ether), Triton X-405 reduced (polyoxyethylene(40) isooctylcyclohexyl ether), Triton X-45 (Polyethylene glycol 4-tert-octylphenyl ether), Triton X-705-70, TWEEN in any form including: TWEEN 20 (Polyoxyethylene sorbitan monolaurate), TWEEN 21 (Polyoxyethylene sorbitan monolaurate), TWEEN 40 (polyoxyethylene(20) sorbitan monopalmitate), TWEEN 60 (Polyethylene glycol sorbitan monostearate), TWEEN 61 (Polyethylene glycol sorbitan monostearate), TWEEN 65 (Polyoxyethylene sorbitan Tristearate), TWEEN 80 (Polyoxyethylene sorbitan monooleate), TWEEN 81 (Polyoxyethylene sorbitan monooleate), TWEEN 85 (polyoxyethylene(20) sorbitan trioleate), Tyloxapol (4-(1,1,3,3-tetramethylbutyl)phenol polymer with formaldehyde and oxirane), and n-Undecyl β-D-glucopyranoside.

11. The method of claim 1, wherein the detergent is an anionic detergent.

12. The method of claim 11, wherein the anionic detergent is selected from the group consisting of Chenodeoxycholic acid, Cholic acid, Dehydrocholic acid, Deoxycholic acid, Digitonin, Digitoxigenin, N, N-Dimethyldodecylamine N-oxide, Sodium docusate, Sodium glycochenodeoxycholate, Glycocholic acid, Glycodeoxycholic acid, Glycolithocholic acid 3-sulfate disodium salt, Glycolithocholic acid ethyl ester, N-Lauroylsarcosine, Lithium dodecyl sulfate, Lugol (Iodine Potassium Iodide), Niaproof (2-Ethylhexyl sulfate sodium salt), Niaproof 4 (7-Ethyl-2-methyl-4-undecyl sulfate sodium salt), optionally substituted alkylsulfonate salts (including salts of 1-butanesulfonate, pentanesulfonate, hexanesulfonate, 1-Octanesulfonate, 1-decanesulfonate, 1-dodecanesulfonate, 1-heptanesulfonate, 1-heptanesulfonate, 1-nonanesulfonate, 1-propanesulfonate, and 2-bromoethanesulfonate, especially the sodium salts), Sodium cholate, Sodium deoxycholate, optionally substituted Sodium dodecyl sulfate, Sodium octyl sulfate, Sodium taurocholate, Sodium taurochenodeoxycholate, Sodium taurohyodeoxycholate, Taurolithocholic acid 3-sulfate disodium salt, Tauroursodeoxycholic acid sodium salt, Trizma dodecyl sulfate, Ursodeoxycholic acid, a salt of any thereof, and an acid of any thereof.

13. The method of claim 1, wherein the detergent is a cationic detergent.

14. The method of claim 13, wherein the cationic detergent is selected from the group consisting of Alkyltrimethylammonium bromide, Benzalkonium chloride, Benzyldimethylhexadecylammonium chloride, Benzyldimethyltetradecylammonium chloride, Benzyldodecyldimethylammonium bromide, Benzyltrimethylammonium tetrachiorojodate, Dimethyldioctadecylammonium bromide, Dodecylethyldimethylammonium bromide, Dodecyltrimethylammonium bromide, Ethyihexadecyldimethylammonium bromide, Girard's reagent T, Hexadecyltrimethylammonium bromide, N,N',N'-Polyoxyethylene(10)-N-tallow- 1,3-diaminopropane, Thonzonium bromide, and Trimethyl(tetradecyl)ammonium bromide.

15. The method of claim 14, wherein the cationic detergent is benzalkonium chloride.

16. The method of claim 1, wherein the detergent is a zwitterionic detergent.

17. The method of claim 16, wherein the zwitterionic detergent is selected from the group consisting of CHAPS (3-{(3-cholamidopropyl)-dimethylammonio}-1-propanesulfonate), CHAPSO (3-{(3-chotamidopropyl) dimethylammonio}-2-hydroxy-1-propane-sulfonate), 3-(Decyldimethylammonio) propanesulfonate, 3-(Dodecyldimethylammonio) propanesulfonate, 3-(N,N-Dimethylmyristylammoni- o) propanesulfonate, 3-(N,N-Dimethyloctadecylammonio) propanesulfonate, 3-(N,N-Dimethyloctylammonio) propanesulfonate, and 3-( N,N-Dimethylpalmityl-ammonio)propanesulfonate.

18. The method of claim 17, wherein the zwitterionic detergent is CHAPS.

* * * * *